(12) United States Patent
Liljenberg et al.

(10) Patent No.: US 9,772,311 B2
(45) Date of Patent: Sep. 26, 2017

(54) ACTIVE ACOUSTIC METHOD FOR PREDICTING PROPERTIES OF PROCESS FLUIDS COMPRISING SOLID PARTICLES OR GAS/LIQUID VOLUMES BASED ON THEIR SIZE DISTRIBUTION AND CONCENTRATION

(71) Applicant: ACOSENSE AB, Vastra Frolunda (SE)

(72) Inventors: Thomas Liljenberg, Västerås (SE); Stevan Backa, Karlstad (SE); Lennart Thegel, Västerås (SE); Mats Åbom, Järfälla (SE)

(73) Assignee: ACOSENSE AB, Vastra Frolunda (SE)

( * ) Notice: Subject to any disclaimer, the term of this patent is extended or adjusted under 35 U.S.C. 154(b) by 160 days.

(21) Appl. No.: 14/524,634

(22) Filed: Oct. 27, 2014

(65) Prior Publication Data
US 2015/0059442 A1    Mar. 5, 2015

Related U.S. Application Data

(63) Continuation-in-part of application No. 10/332,955, filed as application No. PCT/SE01/01565 on Jul. 6, 2001.

(30) Foreign Application Priority Data

Jul. 14, 2000    (SE) ...................... 0002667

(51) Int. Cl.
*G01N 29/032*    (2006.01)
*G01N 29/46*    (2006.01)

(52) U.S. Cl.
CPC ........... *G01N 29/032* (2013.01); *G01N 29/46* (2013.01); *G01N 2291/014* (2013.01);
(Continued)

(58) Field of Classification Search
CPC .... B01J 2219/00362; B01L 2400/0436; B01L 2200/143; B01L 2400/0439;
(Continued)

(56) References Cited

U.S. PATENT DOCUMENTS 3,710,615 A    1/1973    Johnson et al.
3,914,984 A    10/1975   Wade
(Continued)

FOREIGN PATENT DOCUMENTS

EP    2075579 A2    7/2009
FR    2772476 A1    6/1999
(Continued)

OTHER PUBLICATIONS

H. Martens et al., Multivariate Calibration, pp. 116-163, 1989.
(Continued)

*Primary Examiner* — Yelena G Gakh
(74) *Attorney, Agent, or Firm* — Buchanan Ingersoll & Rooney P.C.

(57) ABSTRACT

In the present invention a controllable acoustic source (14) in connection with the process fluid (10) emits a signal (18) into the fluid (10), consisting of a suspension of particles (12), being volumes of gas, liquid or solid phase. The controllable acoustic signal (18) is allowed to interact, with the particles (12), and the acoustic (pressure) signals (22) resulting from such an interaction is measured preferably via a sensor (24). A spectrum is measured. The spectrum is used to predict properties, content and/or size of the particles (12) and/or used to control a process in which the process fluid (10) participates. The prediction is performed in the view of the control of the acoustic source (14). The used acoustic signal has preferably a frequency below 20 kHz.

11 Claims, 13 Drawing Sheets

(52) U.S. Cl.
CPC ........... *G01N 2291/0222* (2013.01); *G01N 2291/02416* (2013.01); *G01N 2291/02433* (2013.01); *G01N 2291/02836* (2013.01); *G01N 2291/02872* (2013.01)

(58) Field of Classification Search
CPC ....... B01L 2200/148; B01L 2200/0636; B01L 2200/0652; B01L 3/502761; B41J 2/04575; G01F 23/296; G01F 23/2968; G01F 1/712; G01F 23/29
See application file for complete search history.

(56) References Cited

U.S. PATENT DOCUMENTS

| | | | |
|---|---|---|---|
| 4,228,636 | A | 10/1980 | Homburg |
| 4,445,389 | A | 5/1984 | Potzick et al. |
| 4,574,624 | A | 3/1986 | Lehtinen et al. |
| 4,763,307 | A | 8/1988 | Massa |
| 5,040,734 | A | 8/1991 | Belchamber et al. |
| 5,056,357 | A | 10/1991 | Dymling et al. |
| 5,121,629 | A | 6/1992 | Alba |
| 5,126,513 | A | 6/1992 | Wang et al. |
| 5,628,937 | A | 5/1997 | Oliver et al. |
| 5,714,691 | A | 2/1998 | Hill |
| 5,831,150 | A | 11/1998 | Sowerby et al. |
| 5,976,466 | A | 11/1999 | Ratner et al. |
| 6,029,507 | A | 2/2000 | Faber et al. |
| 6,354,147 | B1 | 3/2002 | Gysling et al. |

FOREIGN PATENT DOCUMENTS

| | | |
|---|---|---|
| WO | WO 91/10904 A1 | 7/1991 |
| WO | WO 97/06433 A1 | 2/1997 |
| WO | WO 99/15890 A2 | 4/1999 |
| WO | WO 00/00793 A1 | 1/2000 |

OTHER PUBLICATIONS

M. Karras et al., "Pulp Suspension Flow Measurement Using Ultrasonics and Correlation", 1982 Ultrasonics Symposium, 1982 IEEE, pp. 915-918.

D.J. Adams, PhD. MSc., "Ultrasonic Propagation in Paper Fibre Suspensions", pp. 187-194, *3rd International IFAC Conference on Instrumentation and Automation in the Paper, Rubber and Plastics*, May 1976.

J. Sundholm, Papermaking Science and Technology, Book 5, Mechanical Pulping, 1999, pp. 125-138.

A. Lohrmann, "Monitoring sediment concentration with acoustic backscattering instruments", Norteck Technical Note No. 3, pp. 1-5.

Lee et al., "Highly-efficient broadband acoustic transducer for all-fiber acousto-optic devices", Electronic Letter, Sep. 2003, v. 39, No. 18, pp. 1-2.

European Patent Office Communication—dated Aug. 30, 2007.

Spelt et al., "Determination of particle size distributions from acoustic wave propagation measurements", Physics of Fluids, May 1999, v. 11, No. 5, pp. 1065-1080.

Halstensen et al., New developments in acoustic chemometric prediction of particle size distribution—'the problem is the solution', J. Chemom., 2000, v. 14, pp. 463-481.

McClements, "Ultrasonic Measurements in Particle Size Analysis", Encyclopedia of Analytical Chemistry, Ed. Robert A. Meyers. John Wiley & Sons Ltd, Chichester, 2006.

Hayama et al., "Acoustic characteristics of an electrodynamic planar digital loudspeaker using noise shaping technology", J. Acoust. Soc. Am., 2005, v. 117, No. 6, pp. 3636-3644.

A.S. Dukhin et al., "Acoustic electroacoustic spectroscopy for characterizing concentrated dispersions and emulsions", Advances in Colloid and Interface Science, 92 (2001).

M. Ainslie et al., "A simplified formula for viscous and chemical absorption in sea water", 1998 J. Acoustical Society of America, pp. 1671-1672.

A. Bjork et al., "Spectra of wavelet scale coefficients from process acoustic measurements as input for PLS modeling of pump quality", Journal of Chemometrics, 2002, pp. 521-528.

A. Bjork et al., "Modeling of pump quality parameters from distribution curves extrated from process acoustic measurements on a thermo mechanical pump (TMP) process", Chemometrics and Intelligent Laboratory Systems 85 (2007), pp. 63-69.

McClements, "Principles of Ultrasonic Droplet Size Determination in Emulsions", Langmuir, 1996, v. 12, pp. 3454-3461.

Esbensen et al., "Acoustic chemometrics-from noise to formation", Chemometrics and Intelligent Laboratory System, 1998, v. 44, pp. 61-76.

Glynn-Jones et al., "Acoustofluidics 9: Modelling and applications of planar resonant devices for acoustic particle manipulation", Lab Chip, 2012, v. 12, pp. 1417-1426.

Office Action (Communication pursuant to Article 94(3) EPC) dated Dec. 17, 2014, by the European Patent Office in corresponding European Patent Application No. 01 950 141.0-1554. (4 pages).

Office Action (Communication pursuant to Article 94(3) EPC) dated Aug. 10, 2016, by the European Patent Office in corresponding European Patent Application No. 01 950 141.0-1554. (7 pages).

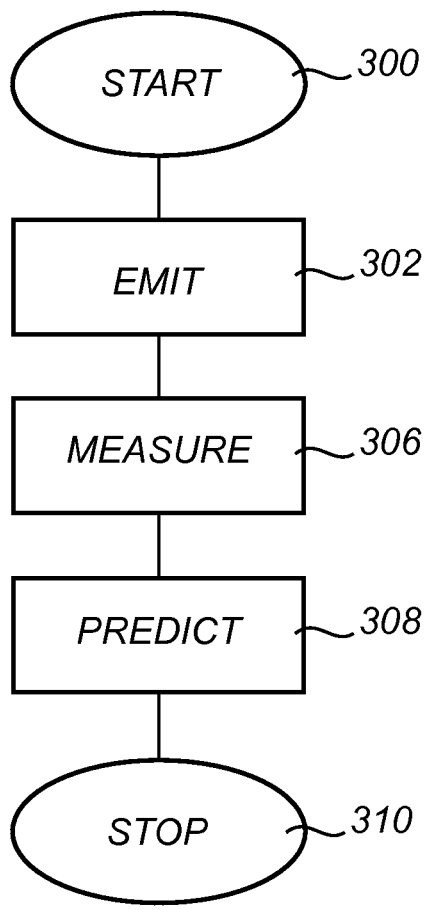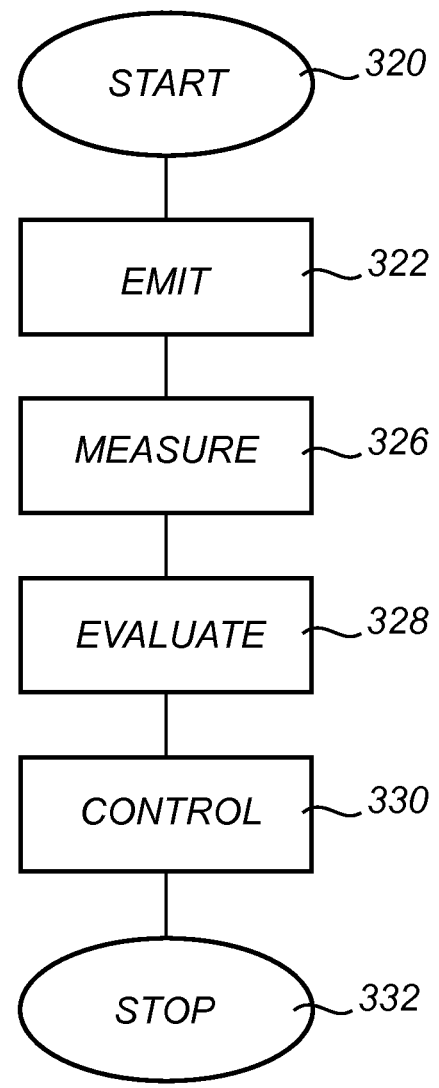
Fig. 2
Fig. 4

ACTIVE ACOUSTIC METHOD FOR PREDICTING PROPERTIES OF PROCESS FLUIDS COMPRISING SOLID PARTICLES OR GAS/LIQUID VOLUMES BASED ON THEIR SIZE DISTRIBUTION AND CONCENTRATION

CROSS REFERENCE TO RELATED APPLICATIONS

The present application is a continuation-in-part of U.S. application Ser. No. 10/332,955, filed on Jun. 17, 2003, which is a U.S. national stage entry of International Application No. PCT/SE2001/001565, filed on Jul. 6, 2001, which claims the benefit of Swedish Application No. SE 0002667-4, filed on Jul. 14, 2000. The entire contents of each of U.S. application Ser. No. 10/332,955, International Application No. PCT/SE2001/001565, and Swedish Application No. SE 0002667-4 are hereby incorporated herein by reference in their entirety.

TECHNICAL FIELD

The present invention generally relates to methods for monitoring properties of process fluids (gases or liquids) by acoustic analysis and devices for performing the method. The present invention also relates to process systems involving process fluids and methods for controlling the systems, based on acoustic analysis. In particular, the present invention is directed to process fluids having suspended or emulgated gas, liquid or solid volumes, i.e., multi-phase fluids. In the following description this will simply be referred to as "a fluid having suspended particles", even if the "particles" may involve gas or liquid phases.

BACKGROUND

In many production process systems, a fluid having suspended particles is used, either as a raw material, an intermediate product or a final product. Examples may be found in widely differing areas, such as pulp or paper industries, pharmaceutical industries, food processing, building material fabrication, etc. Common for many of the processes is that the inherent properties, size or concentration of the suspended particles are of crucial importance for the final product. Therefore, there is a general desire to find methods for analyzing the properties of the particles in a fast, accurate, safe, cheap and easy manner in order to predict the final product quality and to be able to control the processing steps accordingly.

Some basic types of measurement philosophies exist for process fluids; "off-line", "on-line", "at-line" and "in-line".

The classical off-line procedure is to extract samples of the process fluid for analysis in a laboratory. However, in this way only a part of the process fluid is analyzed, and the possible feedback of such an analysis is generally slow.

An analysis method suitable for providing data for control purposes has to be performed in direct contact with the actual process fluid flow.

To speed up the off-line procedure (up to 5-10 times) an on-line procedure with automatic sampling systems have been developed in which measurements based on, e.g., optical measurement techniques are used. Typically such systems operate by diverting a small portion of the process fluid into a special pipe or volume. One example being the PQM system (Pulp Quality Monitor) from Sunds Defibrator, which measures freeness, fiber length and shive content in a pulp suspension. A common problem with all off-line and some on-line and at-line methods is that only a part of the flow is measured. The properties in such a diversion flow may differ from the main flow. TCA (Thermomechanical pulp Consistency Analyser) from ABB AB measures the consistency of the pulp. The system is using fiber optic techniques. Other similar systems are the Smart Pulp Platform (SPP™) available from ABB, and "Fiber Master" developed by the Swedish pulp and paper research institute (STFI).

In-line methods, which operates directly on the entire process fluid without extracting fluid into a special test space, are generally faster than off-line methods and can reduce some of the problems listed for these methods. However, mechanical devices have to be inserted in the process line in order to extract the flow sample, which may disturb the main flow and which makes maintenance or replacement work difficult. Furthermore sensors may be contaminated, or the flow may be contaminated by the sensors.

An alternative to use optical or electromagnetic waves is to use mechanical (acoustical) waves. This has several advantages. Acoustic waves are environmentally friendly and also unlike electromagnetic waves they can propagate in all types of fluids.

In the article "Ultrasonic propagation in paper fiber suspensions" by D. J. Adams, 3rd International IFAC Conference on Instrumentation and Automation in the Paper, Rubber and Plastics Industries, p. 187-194, Noordnederlands Boekbedrijf, Antwerp, Belgium, it is disclosed to send ultrasonic beams of frequencies between 0.6 MHz and 15 MHz through a suspension of fibers and the attenuation as well as the phase velocity can be measured as a function of frequency, It is by this possible to obtain information about fiber concentration, size and to some extent the fiber state. However, an elaborate calibration procedure is necessary in order to make the method operable.

In "Pulp suspension flow measurement using ultrasonics and correlation" by M. Karras, E. Harkonen, J. Tornberg and O. Hirsimaki, 1982 Ultrasonics Symposium Proceedings, p. 915-918, vol. 2, Ed: B. R. McAvoy, IEEE, New York, N.Y., USA, a transit time measurement system is disclosed. The system measures primarily the mean flow velocity and tests from various pulp suspensions are described. Doppler shift measurements are used to determine velocity profiles. A frequency of 2.5 MHz was used.

In U.S. Pat. No. 3,710,615, a device and method for measuring of particle concentrations in fluids is disclosed. An acoustic wave of one wavelength is emitted into a fluid containing particles. The amplitude of the acoustic signal is registered and the attenuation of the acoustic signal is deduced. Based on this attenuation, a particle concentration is determined. One embodiment where two frequencies are used is also described. Frequencies of 1 MHz and 200 kHz are mentioned.

In U.S. Pat. No. 5,714,691, a method and system for analyzing a two phase flow is presented. An ultrasonic signal is introduced in a two phase flow and the echo signals are registered by a set of sensors. The flow rate and flow quality is determined based on these measurements. Furthermore, the results are used for regulate the flow. Excluding flow characteristics are discussed.

In the French patent publication FR 2 772 476 a method and a device for monitoring phase transitions are described. The method uses measurements of wave propagation velocities to estimate viscoelastic properties of e.g. milk products, which are subjects to phase transitions. Preferred frequencies are above 10 kHz.

In the international patent application WO 99/15890 a method and a device for process monitoring using acoustic measurements were disclosed. Inherent acoustical fields in the system (up to 100 kHz) are recorded indirectly via wall vibration measurements on a conveyor line, through which a fiber suspension flows. The recordings are graded by a data manipulation program according to predetermined characteristics and a vibration characteristics is generated. Stored vibration characteristics related to earlier recordings are compared at each recording for correlation to the properties of the suspension. The recorded vibrations can be used for controlling the process in a suitable way, for raising alarms at fault situations or for showing changed tendencies.

In the international patent application WO 00/00793, measurements of fluid parameters in pipes are presented. A speed of sound is determined by measuring acoustic pressure signals at a number of locations along the pipe. From the speed of sound, other parameters, such as fluid fraction, salinity etc. can be deduced. Frequencies below 20 kHz are used. Preferably, the method operates only on noise created within the system itself. However, an explicit acoustic noise source may be used.

Since the method used in the above patents is based on a method which makes use of inherently appearing vibrations, or other noise signals, a number of problems result. One being that not only will sound generated in the fluid be picked up but also vibrations from mechanical sources, e.g., pumps, connected to the fluid. This leads to large amounts of disturbances, which increases the amount of averaging or over-determination. Furthermore, since there are no control of the source process methods for suppressing disturbances are difficult to apply. In addition the suggested method must be calibrated for each individual site, since the inherent vibrations are site dependent. This last aspect is a considerable practical limitation since it will cause very large losses in production upon installation.

SUMMARY

A general object of the present invention is to improve the characterization of a process fluid and thereby to control the process in which the process fluid takes part. One object of the present invention is therefore to eliminate the system specificity. This will make the identification independent of the rest of the system and calibration will not depend on the location but only on the process fluid involved. Another object is to improve the ratio "signal-noise" or "signal-disturbances" in system identification measurements. Yet another object of the present invention is to clarify the relations between measured signals and properties of the process fluid. A further object is also to make the data treatment of measurement more efficient.

In general words, a controllable acoustic source in contact with the process fluid emits an acoustic signal into the fluid, consisting of a suspension of particles. "Particles" are in the present application generally defined as volumes of gaseous, liquid or solid phase. Preferably, volumes of a phase different from the fluid is considered. The controllable acoustic signal, controllable by frequency, amplitude, phase and/or timing, interacts with the particles, and a spectrum of the acoustic signals (pressure, wall vibrations) resulting from such an interaction is measured via a sensor. The measured spectrum is correlated to properties, content and/or size of the particles and/or used to control a process in which the process fluid participates. The correlation is performed in view of the control of the acoustic source. The measured spectral component has preferably a wave length that is large compared to the typical size of the process fluid particles and distance between the process fluid particles. The used acoustic signal is typically of a frequency below 20 kHz.

Since the emitted acoustic signal is controllable, by amplitude, frequency, phase and/or time-delay, the controllable acoustic signal can be selected to emphasize acoustic behaviors of the particles/volumes in the process fluid, e.g. by tuning the frequency to characteristic frequencies of the particles/volumes. Furthermore, the signal can comprise one or several single frequencies or frequency bands, which also may vary with time. The controllable acoustic signal may also be emitted during limited time intervals or being amplitude modulated, which enables different noise and disturbance removal procedures on the measured acoustic signals in order to increase the signal/noise ratio.

By measuring not only frequency and corresponding amplitude of the resulting acoustic signal, but also phase, time or spatial dependencies, statistical modeling based on, e.g., multivariate analysis or neural networks may be utilized to make the analysis further robust. The spatial dependence is realized by using special geometric arrangements of sensors along and/or perpendicular to the flow direction.

According to the present invention, information from the measured acoustic signals may also be used for controlling different sub-processes in a process system. The measurements may be performed upstream of a sub-process in order to characterize the process fluid entering the sub-process, i.e. feed-forward information, and/or downstream of a sub-process in order to provide feedback information about the result of the sub-process.

The methods and devices are suitable for use in e.g. paper pulp processes, and may e.g. be used to control the operation of a refiner.

The advantages with the present invention is that it provides a monitoring and/or controlling method which is non-destructive, environmentally friendly and provides, depending on the averaging necessary, data in "real-time". The controllability of the acoustic source and the possibility to tune the frequency to a specific range makes it possible to emphasize important spectral characteristics of the process fluid and allows for noise and disturbance reduction. Furthermore, with a controllable acoustic source different acoustic propagation paths can be excited and used for analysis purposes. The present invention also provides the opportunity for multi-component analysis and can be utilized for different material phases. No sample treatment is involved and the new method has the potential of being possible to use within a large concentration range and also at high temperatures. Finally, laboratory tests have demonstrated the feasibility of the method to perform "real-time" measurements of size and stiffness for cellulose fibers.

Further advantages and features are understood from the following detailed description of a number of embodiments.

BRIEF DESCRIPTION OF THE DRAWINGS

The invention, together with further objects and advantages thereof, may best be understood by making reference to the following description taken together with the accompanying drawings, in which:

FIG. 2 is a flow diagram of a system identification process according to the present invention;

FIG. 4 is a flow diagram of a process control method according to the present invention;

DETAILED DESCRIPTION

Figure 1:
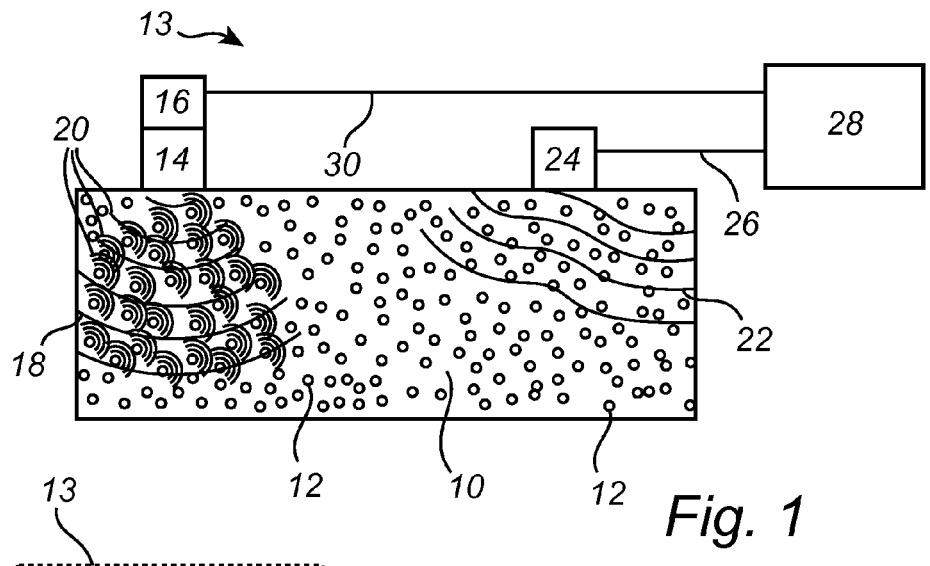
FIG. 1 is a schematic drawing of an analyzing device according to the present invention.

FIG. 1 illustrates an analyzing device 13 for a process system involving a process fluid 10. The process fluid 10 comprises suspended particles 12 of gas, liquid or solid phase. The process fluid may e.g. be a gas containing solid particles, a gas containing liquid droplets, a suspension of solid particles in a liquid, an emulsion of liquid droplets in another liquid, a liquid containing gas volumes or any combination of such fluids. An analyzing device 13 is used to evaluate the properties of the process fluid 10 and the particles 12 therein. The analyzing device comprises an emitter 14, which constitutes an acoustic signal source, and a control unit 16 for operating the emitter 14. The emitter 14 is arranged to emit acoustic signals into the process fluid 10. Acoustic signals 18 are propagating as waves through the process fluid 10 and will then be influenced by the presence of the suspended particles 12.

This influence will, for waves with a wavelength much larger than the size of the particles and distance between them, mainly manifest itself as a changed fluid compressibility. This will lead to a change in the phase speed and to absorption of the acoustic signals 18 which will be frequency dependent. In particular, large changes can be expected in frequency ranges where the suspended particles 12 exhibit resonant vibration behavior. The resonance frequencies depend, e.g., on density, dimensions, stiffness, bonding within the particle and bonding between particles and many other properties. This frequency range is for almost all practical applications located in the audible sub-ultrasonic region, i.e. below 20 kHz. Since the influence of even small particle concentrations, e.g. air bubbles in water, on fluid compressibility can be very large, a method based on long waved acoustic signals is potentially very sensitive for detecting fluid mix variations. Of course this high sensitivity also implies that special measures might be needed to control any unwanted influence on the fluid properties. This can be achieved by applying special signal processing techniques, as discussed further below.

Furthermore, by using frequencies well below the ultrasonic range coherent signals can be provided making measurements of both amplitude and phase response possible. This is described further in detail below.

The particles 12 will thus influence the acoustic transmission properties (phase speed) of the process fluid and absorb vibration energy and thereby change the originally emitted acoustic signals. The vibrating particles 12 will also themselves emit energy in the form of acoustic signals 20. These signals will typically be in the same frequency range as the particle vibrations, i.e. in the frequency range below the ultrasonic range. The modified emitted acoustic signals 18 from the emitter 14 and the acoustic signals emitted from the particles 20 will together form a resulting acoustic signal 22.

An acoustic signal sensor 24 is arranged at the system for measuring acoustic signals in the process fluid 10. At least one component of the acoustic spectrum of the acoustic signals is measured. These acoustic signals are the resulting signals 22 from the interaction between the emitted acoustic signals 18 and the particles 12. Since the interaction between acoustic signals and the particles 12 is indicative of the nature of the particles 12, the measured acoustic signals comprise information related to the particles 12 suspended in the process fluid 10. The analyzing device further comprises a processor 28, which is connected to the sensor 24 by a sensor connection 26. The processor 28 is an evaluation unit arranged for correlating the measured acoustic signals to properties, content or distribution of the particles 12 within the process fluid 10. The emitter control unit 16 is preferably controllable by the processor 28 through an emitter connection 30 in order to tune or control the emitted acoustic signals dependent or coordinated with the measurement operation.

In a typical case, the processor 28 operates according to a certain model of the involved system. The model is preferably based on theories about the physical interaction between the particles and the acoustic waves. The model or parameters in the model are calibrated by using a set of acoustic signal measurements and corresponding laboratory measurements of the particle properties of interest. The model is then possible to use for predicting the particle properties from acoustic spectra of unknown samples. Specific examples of how a model may be derived are given below.

A corresponding method for system identification is illustrated in the flow diagram of FIG. 2. The procedure starts in step 300. In step 302, an acoustic signal of sub-ultrasonic frequencies is emitted into a process fluid comprising suspended particles. The acoustic signals interact with the suspended particles and give rise to a resulting acoustic signal. This resulting acoustic signal is measured in step 306 and in step 308, the measurement results are used to predict the properties of the particles in the fluid e.g. according to a pre-calibrated model. The predicted properties are preferably mechanical or chemical data, concentrations, distributions and sizes of the particles. If the system identification is performed in a process system, the prediction may also be connected to properties of products manufactured by the process fluid. The procedure ends in step 310.

Figure 3A:
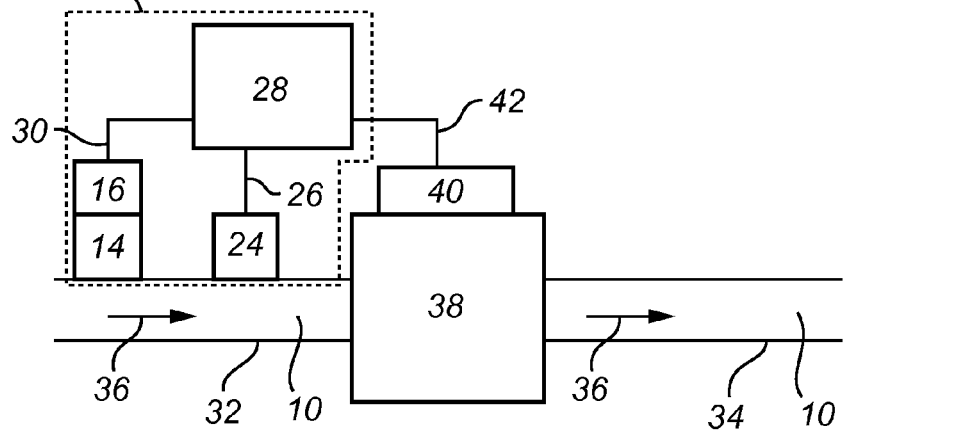
FIGS. 3a and 3b are schematic drawings of process control systems according to the present invention providing feed-forward and feed-back, respectively.

FIG. 3a illustrates a general process system involving a process fluid 10. A flow inlet 32 guides the process fluid 10 into a subprocess device 38, in which the process fluid is influenced. The process fluid 10, typically in a modified state, leaves the subprocess device 38 in a flow outlet 34. The process fluid thus flows in the direction of the arrows 36, from the left to the right in FIG. 3a. An analyzing device 13 as described above is arranged on the upstream flow inlet 32, and is arranged to analyses particles within the process fluid 10, before the process fluid enters the subprocess device 38. The processor 28 uses acoustic spectrum information to predict properties of the particles of the process fluid 10 e.g.

according to a pre-calibrated model. Properties, which are of importance for the following subprocess, can thereby be monitored. An operator can e.g. use this information to control the subprocess accordingly or the values of the predicted particle properties can be used as input parameters in available conventional process control means.

A process control unit 40 controls the operation parameters of the subprocess and is connected by a control connection 42 to the processor 28 of the analyzing device 13. By supplying the processor 28 with information about how the parameter settings of the subprocess influence the properties of the process fluid particles, the processor 28 will be able to provide the process control unit 40 with appropriate control information, based on the actual properties of the particles. This information can e.g. be used by an operator to control the subprocess to give particles with certain predetermined properties accordingly. Alternatively, the processor 28 provides values of the predicted particle properties to the process control unit 40 as input parameters. A feed-forward control is thus accomplished.

Figure 3B:
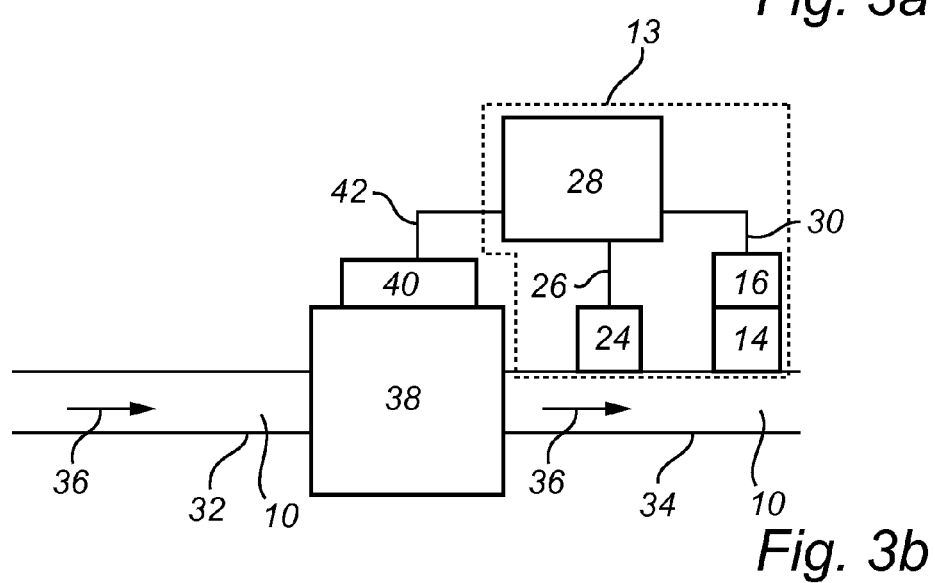

FIG. 3b illustrates another set-up of a general process system involving a process fluid 10. This system comprises the same units and parts as in the previous set-up, but arranged in a slightly different manner. Here, the analyzing device 13 with its emitter 14 and sensor 24 is arranged on the downstream flow outlet 34, and is arranged to analyses particles within the process fluid 10, after the process fluid leaves the subprocess device 38. The processor 28 uses acoustic spectrum information to predict properties of the particles of the process fluid 10 e.g. according to a pre-calibrated model. Properties, which are of importance for how the subprocess has been performed, can thereby be monitored. An operator can e.g. use this information to control the subprocess accordingly or the values of the predicted particle properties can be used as input parameters in available conventional process control means.

A process control unit 40 controls the operation parameters of the subprocess and is connected by a control connection 42 to the processor 28 of the analyzing device 13. By supplying the processor 28 with information how the parameter settings of the subprocess influence the properties of the process fluid particles, the processor 28 will be able to provide the process control unit 40 with appropriate control information, based on the properties of the particles resulting from the subprocess. Alternatively, the processor 28 provides values of the predicted particle properties to the process control unit 40 as input parameters. A feed-back control is thus accomplished.

Obviously, these two different modes of system control can be combined in any configuration.

A corresponding method for system control is illustrated in the flow diagram of FIG. 4. The procedure starts in step 320. In step 322, an acoustic signal of sub-ultrasonic frequencies is emitted into a process fluid comprising suspended particles. The acoustic signals interact with the suspended particles and give rise to a resulting acoustic signal. This resulting acoustic signal is measured in step 326 and in step 328, the measurement results are evaluated, preferably in terms of properties of the particles in the fluid. The evaluated properties are preferably mechanical or chemical data, concentrations, distributions and sizes of the particles. These properties may also be connected to properties of products manufactured of the process fluid, and a corresponding evaluation for such properties is thus possible to perform. These properties are in step 330 used for controlling a subprocess of the system influencing the process fluid. The procedure ends in step 332.

The controllability of the acoustic source is very important. By selecting amplitude, frequency, phase and/or timing of the acoustic signals, different properties of the particles can be addressed. By controlling the frequency, the acoustic signals may e.g. be tuned to certain resonance frequencies connected to the particles, addressing specific properties. By modulating the amplitude of the signal source, noise reduction may be performed, or time dependent interactions may be emphasized or suppressed. By controlling the phase, dynamic measurements are facilitated. By controlling the timing of the acoustic signals, processes having time dependencies may be investigated. Such investigations are not possible to perform using only passive sources of acoustic signals. A few examples of simplified situations will illustrate the possibilities of controlling the signal source.

Figure 5A:
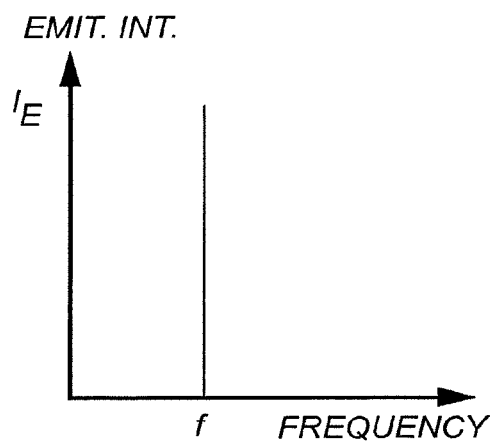
FIGS. 5a-5i are diagrams illustrating examples of emitted acoustic signals or measured acoustic signals in different simplified situations.
Figure 5B:
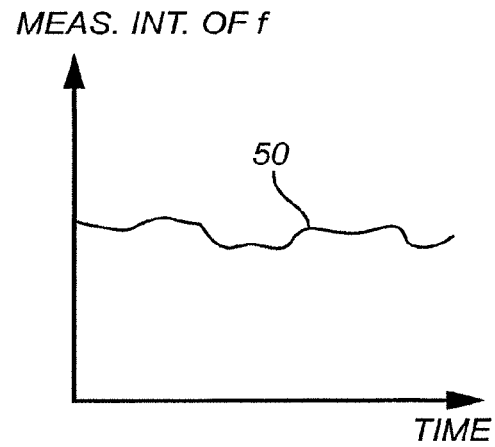

In FIG. 5a, the signal source emits an acoustic signal having one frequency f of intensity $I_E$. The frequency is tuned into a certain frequency corresponding to a characteristic frequency of the particles, e.g. an absorption frequency of particles within the process fluid. The larger density of particles, the larger absorption will result. The acoustic signal is emitted with a constant intensity IE for the time the measurement lasts. By measuring the intensity 50 of the same frequency component of the resulting acoustic signal from the process fluid as a function of time, an indication of the particle density variation with time will be obtained. This is schematically illustrated in FIG. 5b. Using such a measurement, a concentration monitoring is easily performed and by introducing an interval of permitted variations, the signal may easily be used as an indicator of a too high or too low concentration.

Figure 5C:
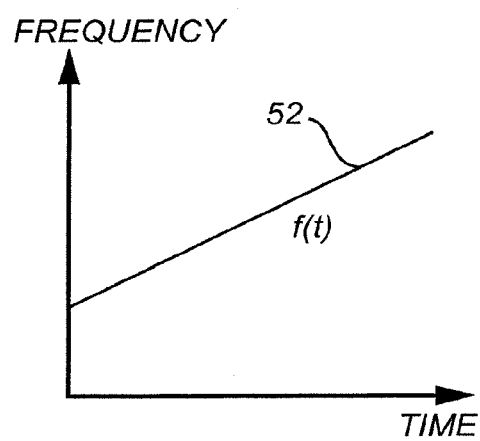
Figure 5D:
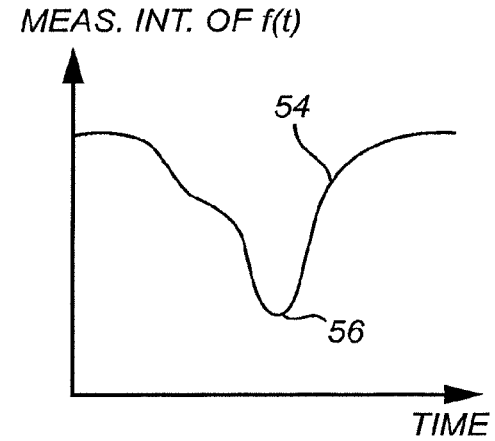

Assuming a process fluid having solid particles of slights differing dimensions. Knowing that a certain resonance vibration is related to a certain dimension of the particle can be used to investigate the size distribution of the particles in the fluid. FIG. 5c illustrates a time dependent emitted acoustic signal. The amplitude or intensity of the signal is kept constant, while the frequency is varied linearly with time, as illustrated by the line 52 in FIG. 5c. The sensor can be operated in a coordinated manner, measuring the intensity of the same frequency that the acoustic source at each occasion emits. In that way, a resulting curve 54 as illustrated in FIG. 5d may be obtained. An intensity minimum 56 at the curve 54 indicates that this frequency corresponds to the median value of the dimension in question. Information about the size distribution is also obtainable.

In this manner, the frequency can be used for revealing different aspects related to the particles. The frequency may thus comprise e.g. a single constant frequency, a single frequency varying with time, a number of single constant frequencies, a number of single frequencies varying with time, or different types of limited frequency bands, such as white or pink noise.

Figure 5E:
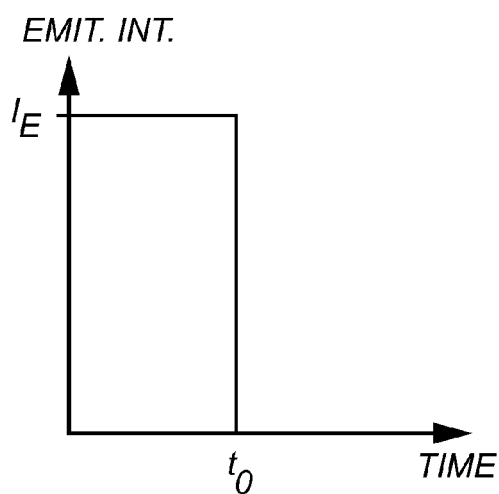
Figure 5F:
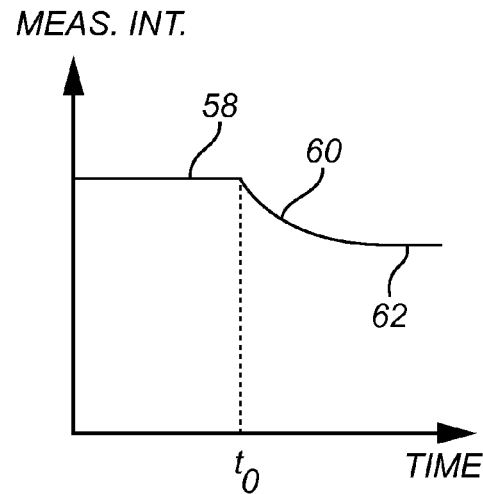

The timing of the emitted acoustic signals may also be used, e.g. by using pulsed acoustic signals emitted during limited time intervals. FIG. 5e illustrates a simplified situation where an acoustic signal is emitted during a time interval up to the time $t_o$, when the emission is turned off. By measuring e.g. an intensity of some acoustic signal features, a curve illustrated in FIG. 5f may be obtained. This curve presents a constant level portion 58 during the time the pulse is emitted. When to is reached, the intensity starts to decrease creating a reverberation process, as shown in the portion 60, until the intensity levels out at 62. An interpretation of this behavior could e.g. be that inherent noise within the system gives rise to an intensity of the signal feature corresponding to the level of the portion 62. This intensity would therefore correspond to background noise. Background signals in the measured acoustic signals may be reduced simply by subtracting acoustic signals measured during time intervals, in which the controllable acoustic source is inactive. The intensity difference between the portions 58 and 62 would therefore more accurately correspond to e.g. some concentration values of particles within the fluid. The detailed behavior of the decreasing portion 60 may also give some information about e.g. mechanical interaction conditions within or around the particles. The slope could e.g. correspond to remaining vibrating particles after the turn-off of the acoustic source.

Figure 5G:
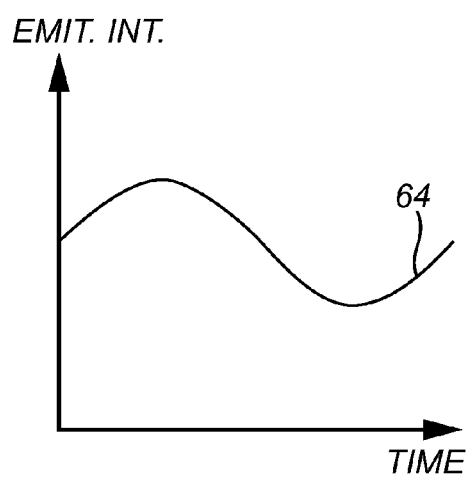
Figure 5H:
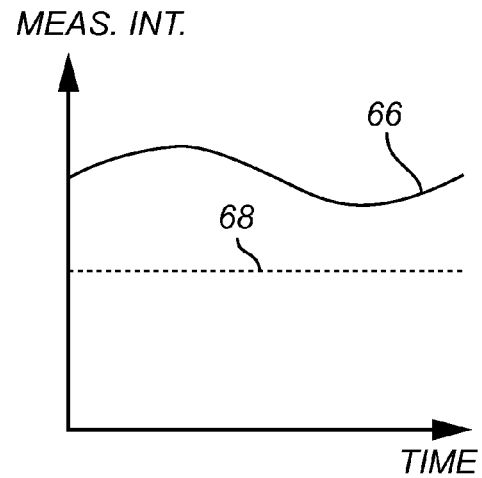

More sophisticated background reduction methods would be available by amplitude modulating the emitted acoustic signal. In FIG. 5g, the intensity of an emitted acoustic signal is varied with time according to the curve 64. A corresponding measured intensity of any acoustic spectrum feature could then vary e.g. as the curve 66 in FIG. 5h. The intensity variation is less pronounced, which implies that a background noise probably is present. By comparing the amplitude variations of the emitted and sensed signals, a background level according to the broken line 68 is found. Thus, background reduction is possible to perform also with continuously emitted signals.

From the above examples, it is obvious that the sensors should be able to measure different properties of the resulting acoustic signals. In a corresponding manner as for the emitted signals, the sensors measure e.g. amplitude, frequency, phase and/or timing of the acoustic signals resulting from the interaction with the particles in the process fluid. It is preferred if the sensors may measure at least three of the above mentioned characteristics, since a robust multivariate analysis then can be performed. The use of more variable dimensions is illustrated by a simplified example.

Figure 5I:
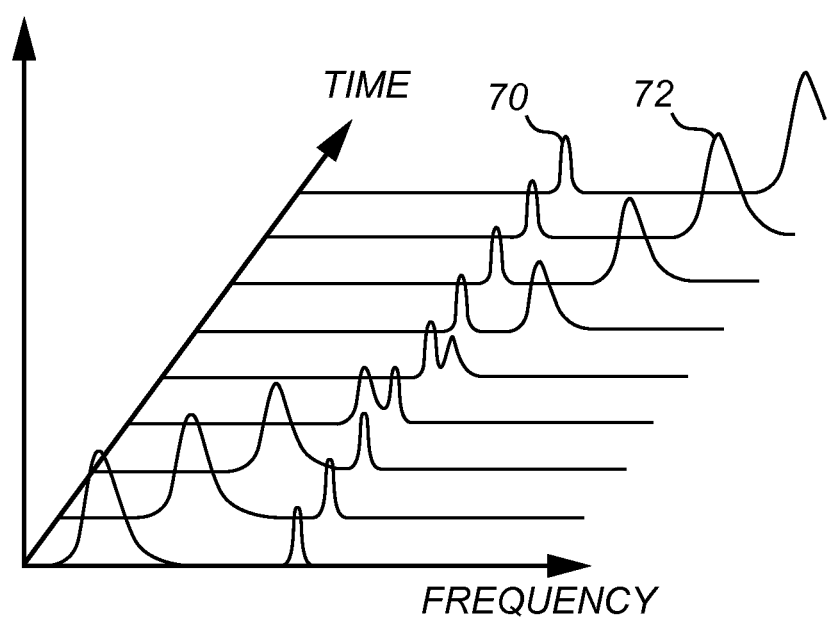

Assume an emitted acoustic signal according to FIG. 5c. A sensor measures an acoustic spectrum within a certain frequency interval at a number of successive times during the emission frequency scan. A possible result is shown in FIG. 5i. Two main components are present in the resulting spectrum. A first component 72 follows the emitted frequency, and a second component 70 is constant in frequency. The result indicates that the particles have a resonance frequency corresponding to a minimum intensity (max absorption) of the first component 72. However, when the emitted frequency corresponds to the second component 70, the two signals are superimposed and an intensity curve like in FIG. 5d would show a peculiar behavior. However, following the evaluation of the spectra, the different features are easily distinguished and a correct analysis may be obtained.

The above examples are only given as oversimplified examples to increase the understanding of the possibilities of a system with controllable active acoustic sources. In real cases the situations are far more complicated and multivariate statistical analysis or neural networks are for instance used to evaluate the measured acoustic spectra.

The recorded acoustic spectra are preferably Fourier transformed to obtain intensity variations as a function of frequency. The acoustic spectra are then preferably analyzed using different kinds of multivariate data analysis. The basics of such analysis may e.g. be found in "Multivariate Calibration" by H. Martens and T. Naes, John Wiley & Sons, Chicester, 1989, pp. 116-163. Commercially available tools for multivariate analysis are e.g. "Simca-P 8.0" from Umetrics or PLS-Toolbox 2.0 from Eigenvector Research, Inc. for use with MATLAB™. PLS (Partial Least Square) methods of first or second order are particularly useful. Neural network solutions, such as Neural Network Toolbox for MATLAB™, are also suitable to use for analysis purposes.

To improve the model predicting ability, a pre-treatment of spectral data is sometimes beneficial. Such a pre-treatment can include orthogonal signal correction or wavelength compression of data. Furthermore, both the real and imaginary part of the acoustic signal can be used in multivariate calculations.

Figure 6A:
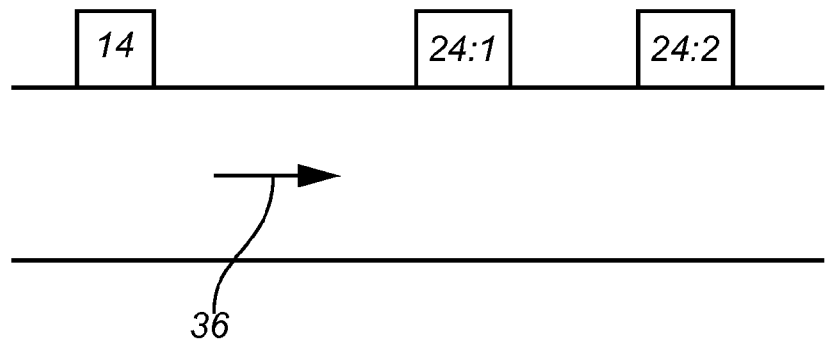
FIGS. 6a-6c are schematic drawings illustrating sensor array configurations.

The relative geometrical positioning and/or the number of emitters and/or sensors can also be used to increase the reliability of the measured signals and thereby the properties of the particles. In FIG. 6a, a flow of process fluid is directed in the direction of the arrow 36. An emitter 14 is arranged in the upstream direction. Two sensors, 24:1, 24:2, are located downstream at different distances from the source. By using measurements from both sensors, additional information may be obtained. One obvious possibility is to measure the propagation speed of the acoustic signals within the fluid or the flow rate, by measuring the phase shift or the time delay between the two measurements. Such information can support the interpretation of other results and may even contain its own information, e.g. the concentration of particles. The distance between the sensors is preferably in the same order of magnitude as the acoustic wavelength to allow for phase measurements. It would also be possible to detect time dependent properties of the particles. If particles are vibration excited or influenced in any other way of an acoustic pulse when passing the emitter, and the result from this excitation or influence will decay with time, the two sensors 24:1 and 24:2 will detect different time behavior of their measurements. From the differences, information about decay times etc. may easily be obtained by computer supported analysis.

Figure 6B:
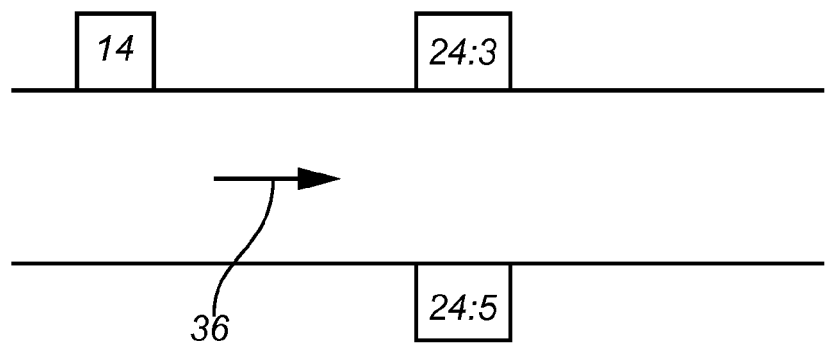
Figure 6C:
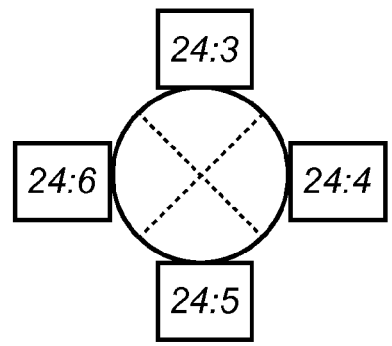

The positioning of sensors can be used also in other ways. In FIG. 6b, a system containing four sensors, of which two are shown in the sectional view along the flow direction, is illustrated. In FIG. 6c, a corresponding cross-sectional view is illustrated. The four sensors 24:3. 24:4, 24:5 and 24:6 are positioned in a plane perpendicular to the flow path 36, asymmetrically with respect to the emitter 14, but symmetrically around the pipe enclosing the process fluid flow path 36. By adding and subtracting signals from the four sensors located at one plane it is possible to extract up to four different acoustic wave types (modes). In addition a combination of the arrangements in FIGS. 6a and 6b is possible.

The acoustic signal emitter can be of different types. One obvious choice for gases is to use loudspeakers. In particular at frequencies of a few hundred Hz up to a few kHz a loudspeaker can generate high power signals without any severe problems. For hot gases or dirty environments, the loudspeaker is preferably provided with cooling facilities and protection devices, respectively. For liquid process fluids, at low and intermediate frequencies, more specially constructed sound sources have to be used. One possibility is e.g. to use an electrodynamic shaker driving a membrane or a light-weight piston.

Sensors, detecting acoustic signals, are readily available in the prior art. Since the quantity of primary interest here is fluctuating pressure, the best alternative is probably to use pressure sensors or transducers. For applications in gases at normal temperatures (<70° C.) standard condenser or electric microphones are preferably used. Some well-known manufacturers are Bruel & Kjaer, Larson & Davies, GRAS. and Rion. These microphone types are sensitive and accurate, but for applications in hot or dirty environments they must be cooled and protected. Also very high levels (>140 dB) can be a problem. An alternative for hot and difficult environments is piezoelectric pressure transducers. These are much more expensive than condenser microphones but can be used up to temperatures of several hundred degrees Celsius. Drawbacks are that the pressure sensitivity is much lower than for condenser microphones and that this transducer type can pick up vibrations. An advantage is that many piezoelectric transducers can be used both in liquids and gases. However, special types for liquids also exist and are normally called hydrophones. A leading manufacturer of piezoelectric transducers is Kiestler.

If measuring the pressure, the sensor has to be in direct contact with the fluid. However, this has some obvious disadvantages since it is necessary to make a hole in a pipe or wall for mounting purposes. An alternative choice of sensors is vibration sensors, which can be mounted on a wall and measure the vibrations induced by the acoustic signals. Here, no direct contact with the fluid is required, why the mounting can be made more flexible and protected. However, a wall mounted vibration transducer will also pick up vibrations caused by other means, e.g. by machines comprised in the system. To some extent these wall vibrations will also radiate sound waves into surrounding fluid, which could be picked up by a pressure transducer, but normally, at least in gas filled systems, this effect represents a much smaller disturbance.

In cases where both amplitude and phase measurements are of interest, further dimensional limitations are put on the sensors and frequencies. In order to be able to detect the phase of an acoustic signal, the sensor has to have a size that is small compared with the wave length of the acoustic signals. This puts in practice an upper limit of the frequency that can be used. If, as an example, the phase is going to be measured by a sensor of around 1 cm in size, the wavelength of the acoustic signal should be in the order of at least 15 cm. The speed of sound in e.g. water is in the order of 1500 m/s, which means that a maximum frequency of 10 kHz can be used. Smaller sensor sizes allows higher frequencies.

As mentioned above, the particles can be of any phase; gas, liquid or solid, and of e.g. gel or sol type. However, the interaction of the acoustic signals with the particles becomes typically particularly intense if the phase of the particle matter differs from the phase of the fluid itself. The main explanation for this is the large variation in compressibility that normally exists between different phases. Thus are solid particles in liquid or gas, liquid particles in gas and gas particles in liquids good measurements targets.

Regarding vibration transducers, the standard choice for all frequencies used in the present invention is so called accelerometers, which typically are piezoelectric sensors that gives an output proportional to acceleration. Regarding manufacturers the ones already listed for condenser microphones also apply in this case.

The analysis device and method according to the present invention can be applied in many various fields. A couple of examples will be described briefly below.

Figure 7:
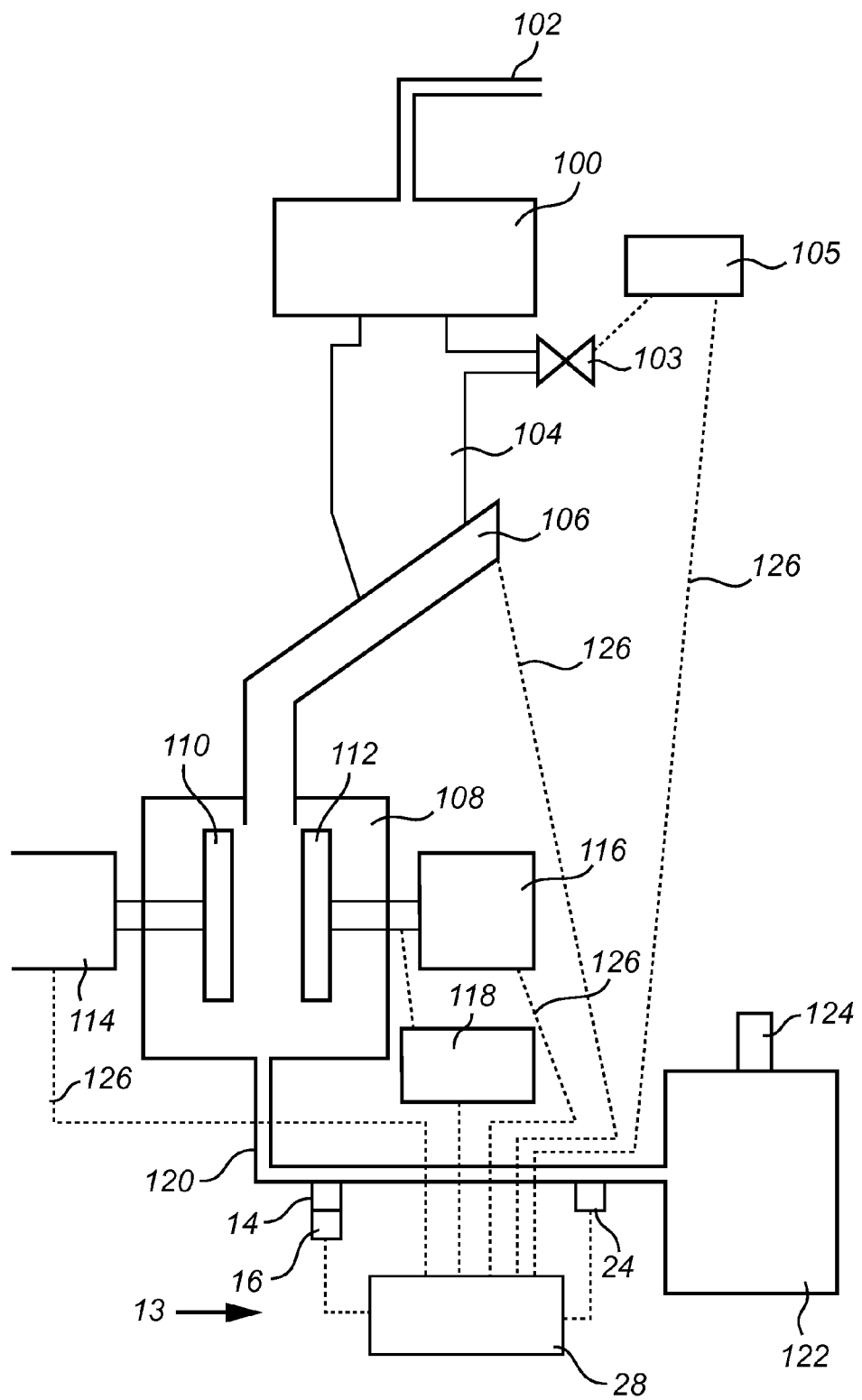
FIG. 7 is a schematic illustration of an embodiment of a refiner line according to the present invention.

In the pulp and paper industry, the acoustic sensor could be installed in all positions where a flow or transportation of pulp is performed. A position of particular interest is in the vicinity of the refiner. The refiner is the most important sub-process step in mechanical pulping and there exist very clear economic benefits for implementation of a more advanced control of the refiner based on new information. FIG. 7 illustrates a typical example of a refiner part of a mechanical pulping process system. A pressurizing unit 100 is supplied with pre-treated wood chips through a supply line 102. The pressurized chips is supplied to a container unit 104, where the chips is mixed with water 105. A screw device 106 brings the mixture with a certain determined rate into a refiner unit 108. The refiner 108 schematically illustrated in FIG. 7 comprises double discs 110, 112, between which the chip mixture is fed. Each disc 110, 112 has a respective motor 114, 116, which applies the necessary rotary motion to the refiner discs 110, 112. A refiner force control device 118 regulates the force with which the refiner discs 110, 112 are pulled together. The chips are mined between the discs, separating the wood fibers.

After refining, the ground pulp fibers suspended in the water mixture exits the refiner at high pressure via an exit pipe 120. The high pressure is reduced, which causes some of the (by the refining process) heated water to evaporate into steam. The steam 124 is separated from the fiber mixture in a cyclone 122 before the fibers are introduced into the following pulping process steps.

An emitter 14 with a control unit 16 is arranged at the exit pipe 120. A sensor 24 is also arranged at the exit pipe a distance from the emitter 14. The emitter 14 and sensor 24 are connected to an evaluation unit 28 comprising a processor. The emitter 14 is controlled to emit acoustic signals into the pulp mixture within the edit pipe 120. The sensor 24 records the resulting acoustic signals and the processor 28 evaluates the results.

Paper strength issues are a vast area with many different laboratory measurement methods and evaluation possibilities. Nevertheless, it is probably the most common and important quality parameter demanded by the customers. Basically, the final paper strength is influenced by three parameters; the single fiber intrinsic strength, the area of fiber-to-fiber bond per length unit of the fiber and the strength of each fiber bond. Longer fibers will provide opportunities for more fiber-to-fiber bonds and therefore the fiber network will be stronger and consequently also the paper. If the fibers are excited, the vibrate with different frequencies depending on their length. The point of self-oscillation will be at a lower frequency for long fibers compared to short ones.

Furthermore, the above property of the refined pulp mixture depends on certain input parameters of the refining process. The first parameter is the type and quality of the wood chips. Such information can be entered into the control system e.g. by an operator. Other parameters which determines the effect of the refining is the water content, the rate in which the chips are entered into the refiner, the disc velocity and the force between the refiner discs 110, 112. The relations between these parameters and the properties of the pulp are normally rather well known, or may be obtained empirically. Based on such relations, the analyzing device 13 may find appropriate changes in the settings of the disc speed, disc force, water content or chip feeding speed by signal connections 126 in order to improve the properties of the resulting fibers. The analyzing device thus constitutes a feed-back system, operating on the final process fluid from the refiner sub-process.

Figure 8:
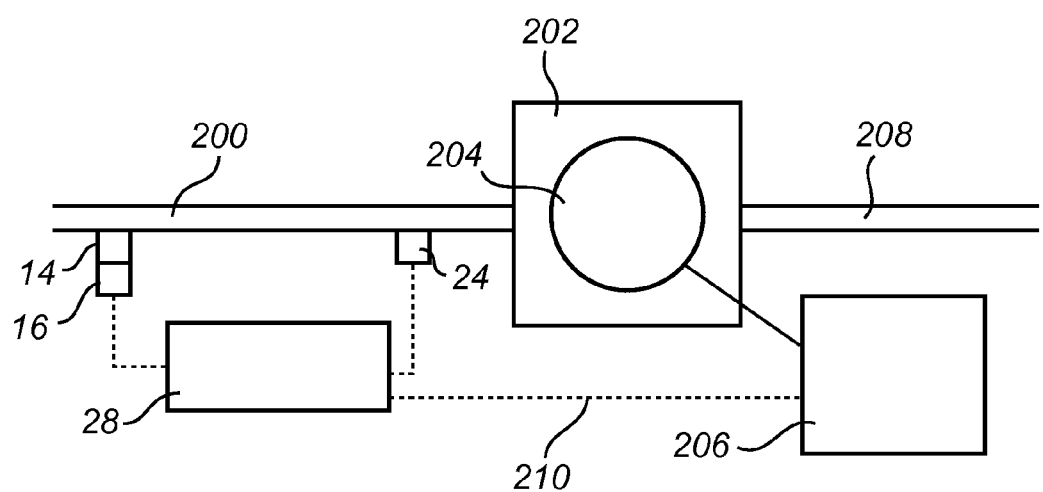
FIG. 8 is a schematic illustration of an embodiment of a pharmaceutical process line according to the present invention.

Another example of a process system for which the present invention is suited is pharmaceutical manufacturing. In certain process lines, liquid particles of active substances are produced in a dilute form and are further processed in a refiner, in order to increase the active substance content. FIG. 8 schematically illustrates a refining sub-process system. An introduction pipe 200 feeds dilute substance fluid into the refiner 202, which comprises separating elements 204. The speed and position of the separating elements 204 determines the ratio between the original active substance content and the final active substance content. A control unit 206 controls the operation of the separator elements. The high concentration fluid leaves the refiner in an exit pipe 208.

The actual concentration of active substance in the original fluid may vary considerably due to production processes that are difficult to control in a totally consistent manner. The operation of the refiner 202 thus has to be adjusted to the differing raw material, i.e. to the actual active substance concentration of the incoming fluid.

An emitter 14 with a control unit 16 is arranged at the introduction pipe 200. A sensor 24 is also arranged at the introduction pipe a distance from the emitter 14. The emitter 14 and sensor 24 are connected to an evaluation unit 28 comprising a processor. The emitter 14 is controlled to emit acoustic signals into the fluid within the exit pipe 120. The sensor 24 records the resulting acoustic signals and the processor 28 evaluates the results.

The active substance exists as small droplets emulgated in the fluid. The substance droplets have different acoustic properties as compared with the remaining part of the fluid. The changing properties makes the droplets in the emulsion to scattering objects for acoustic signals. The scattering properties are determined basically by the droplet size and droplet density. An acoustic signal emitted into the fluid will interact with the substance droplets and result in a resulting acoustic signal, which can be detected. The actual features of the detected signal depends on the droplet size and droplet density, i.e. on the active substance concentration. The processor 28 may therefore evaluate the active substance concentration of the introduced raw fluid. By knowing the relations between the operating conditions of the refiner and the substance concentration ratio, the operation of the refiner can be controlled continuously by the acoustic monitoring, by control connections 210 to the control unit 206, in order to produce a well-controlled active substance concentration in the outgoing process fluid.

The pre-calibrated model referred to above, to be used for predicting properties of a fluid, can for example be established according to the following general procedure:

1) Measuring system properties
2) Creating a linear model from measurements
3) Validating the linear model In step 1), referring to FIG. 1, a measurement signal in the form of a frequency spectrum comprising frequencies between 0-20 kHz having a predetermined amplitude is emitted into the fluid 10 by the emitter 14. The predetermined amplitude may be kept constant while varying the frequency of the signal. Alternatively, the amplitude of the signal source may be modulated during the frequency sweep as discussed above. The transmitted signal is received by the acoustic signal sensor 24 and the received signal will differ from the emitted signal as a result of interaction with the fluid through which the signal propagates. The acoustic signal sensor 24 may, for example, be a piezoelectric sensor, and vibrations in the wall of the pipe may alternately compress and expand the piezoelectric sensor, resulting in a time-varying voltage output from the sensor 24. The time-varying voltage output is digitized, resulting in a vector of voltage values.

Next, the frequency spectrum of the signal output from the sensor 24 is acquired, for example using FFT on the vector of voltage values. The result of the FFT is a vector of values (such as voltage values) representing the amplitude of the vibration in the tank wall, ordered in terms of vibration frequency. This vector is referred to as the frequency spectrum of the signal. To facilitate handling of the very large number of values, the values in the frequency spectrum are summarized for frequency intervals, so-called frequency bins. Conveniently, a frequency bin may correspond to a frequency interval of about 10 Hz.

The received signal may also comprise noise originating from the environment of the measuring apparatus, which may be referred to as passive noise.

The received signal is, following FFT as described above, taken to represent the active acoustic spectrum frequencies (AASF).

When establishing the model, the received acoustic spectra are correlated with reference measurements. Hence, for each emitted signal, a corresponding reference measurement is performed for determining a desired property of the fluid, such as specific surface area of particles in the fluid or fluid viscosity. The reference measurement is typically performed by a conventional measurement method, which is typically a non-acoustic method. Which conventional measurement method is suitably used will, as is well known to one of ordinary skill in the art, depend on the property of the fluid that should be determined. Conventional methods may, for example, include optical refractometer measurements, radioactive measurements, or fluid samples taken from the pipe and analyzed by titration, optical methods or standardized tests, such as the test SCAN-N-22:96 (according to the Scandinavian pulp, paper and board testing committee—http://www.pfi.no/Documents/Scan_test_methods/N/N_22-96.pdf, which is expressly incorporated by reference herein) for determining dry matter content and fiber content in black liquor.

In step 2) (Creating a linear model from measurements), the partial least squares (PLS) method is applied on the AASF together with the corresponding data from reference measurements to reduce the dimensionality of the regressors, thereby making further regression possible. When applying the PLS-method, non-relevant frequencies of the AASF can be sorted out due to low correlation with reference data. Noise cancellation and the discarding of non-relevant information is an intrinsic feature of the PLS dimension reduction method and is commonly used in the field of chemometrics.

Depending on the application, Principal Component Analysis (PCA) may be performed separately on the acoustic spectra and on the reference measurements in order to identify any deviations in the results. The use of PCA for this purpose is, for example, described in detail in the above referenced book "*Multivariate Calibration*" by H. Martens and T. Naes, John Wiley & Sons, Chicester, 1989. Deviating samples (reference measurements and corresponding acoustic spectra) identified using PCA may be removed before applying the above-mentioned PLS-method.

After the PLS method has been applied, linear regression analysis (RA) is applied to determine the parameters $\beta_0$ and $\beta$ of the linear equation:

$$Y=\beta_0+\beta X, \qquad \text{Equation 1}$$

which defines the statistical model. $\beta_0$ and $\beta$ are vectors defining the approximate linear relationship between the amplitudes of the AASF X and reference measurement data Y. The combination of PLS and RA is commonly referred to as Partial Least Squares Regression (PLSR).

In step 3) (Validating the linear model), once $\beta_0$ and $\beta$ values have been established in the calibration phase, the model is validated against reference measurement data (Y) of the particular fluid property of interest measured by a different method, such as a relevant one of the above-mentioned conventional non-acoustic methods. The reference measurements are taken at the same point in time as the AASF-spectra from the acoustic measurement and the well-known procedure of cross-validation is used to determine the validity of the model.

The acoustic spectrum amplitude (X) is multiplied element-wise with the derived property parameters (β) and summed up. Finally the intercept constant $β_0$ is added which results in the prediction $\hat{Y}$. Mathematically this can be expressed as:

$$\hat{Y} = β_0 + \sum_{i=1}^{\#f\ (bins)} X_i β_i \qquad \text{Equation 2}$$

where #f(bins) represents the active acoustic frequency spectrum discretized in bins as described further above. The prediction result $\hat{Y}$ is compared with reference measurement data $Y_{ref}$ to give a measure of the performance of the model.

Figure 9A:
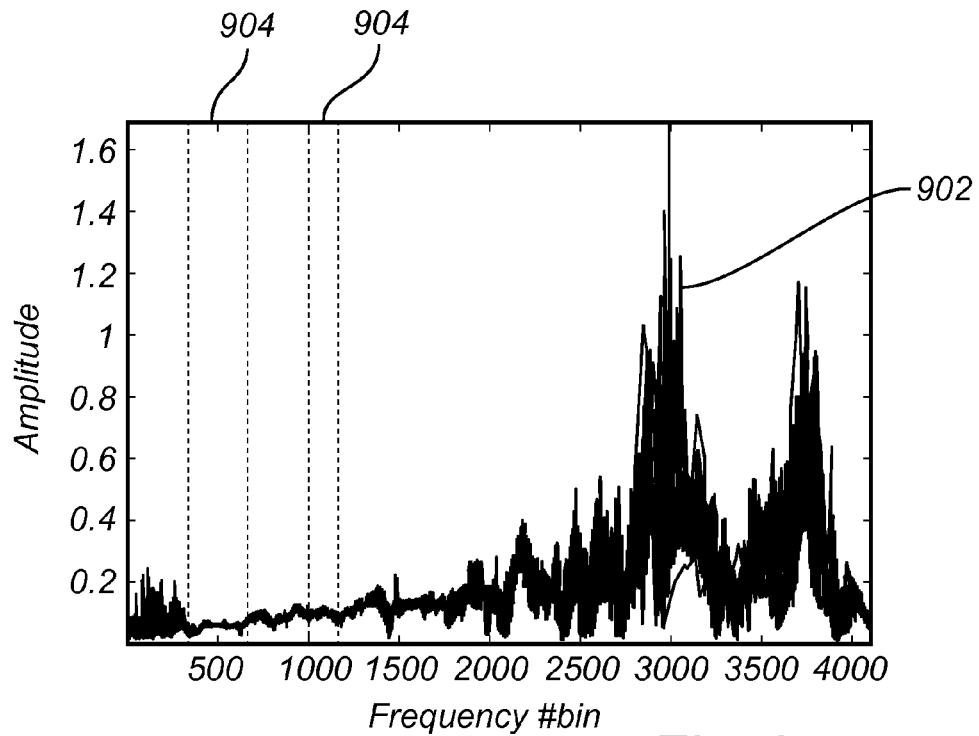
FIGS. 9a-9e are diagrams illustrating examples of the derivation of a model used for predicting properties of a fluid according to various embodiments of the invention.

An illustrative example of the above-described procedure of establishing a pre-calibrated model is shown in FIGS. 9a-9e. FIG. 9a illustrates multiple AASF-spectra 902 where the y-axis shows amplitude and the x-axis shows discretized frequency (#bin), corresponding to a frequency range of about 0 Hz to about 40 kHz. Even though the measurement is performed between 0 and 40 kHz, it is expected that suitable frequencies for characterization can be found between 0 and 20 kHz. The example is taken from a liquor evaporation process step at a paper mill. More specifically, relating to the cross recovery of black- and red liquor part. At this point of the process, both an optical refractometer and a theoretical calculation model were available for validation of the accuracy of the model. In this example, the property of interest is dry matter content in the fluid. The regions 904 illustrate the most relevant acoustic frequencies for this particular installation and property. Accordingly, in some circumstances it may be desirable to only use selected portions of the acquired spectrum for further analysis. In particular, the frequency regions with the highest variation correlated to the fluid property changes can be considered to comprise the frequencies of interest. Frequencies that have high variation which is uncorrelated to variation in fluid properties can be classified as noise.

Figure 9B:
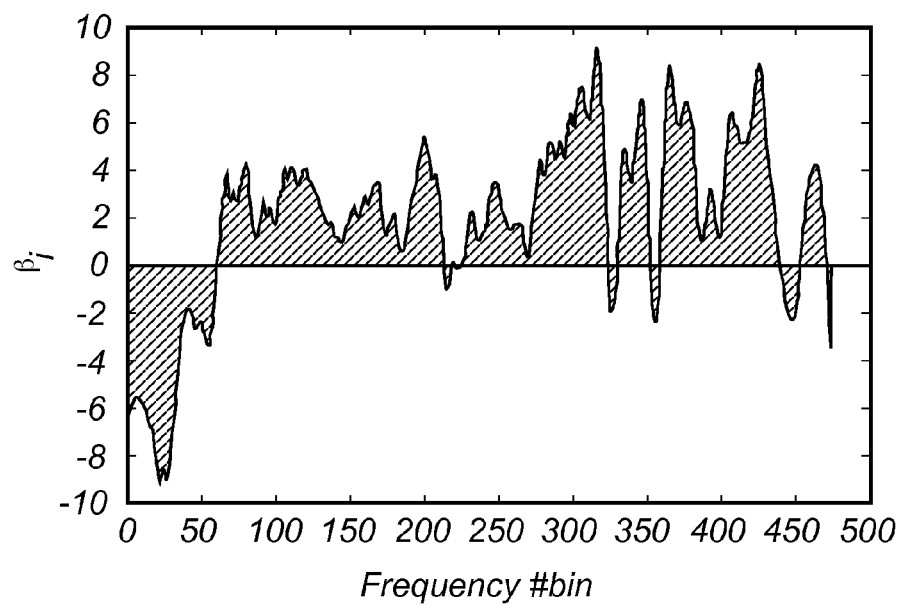

FIG. 9b graphically illustrates the coefficient value $β_i$ (see Equation 2) derived by PLSR from analysis of 40 AASF/ reference values pairs vs. the discretized frequency.

Figure 9C:
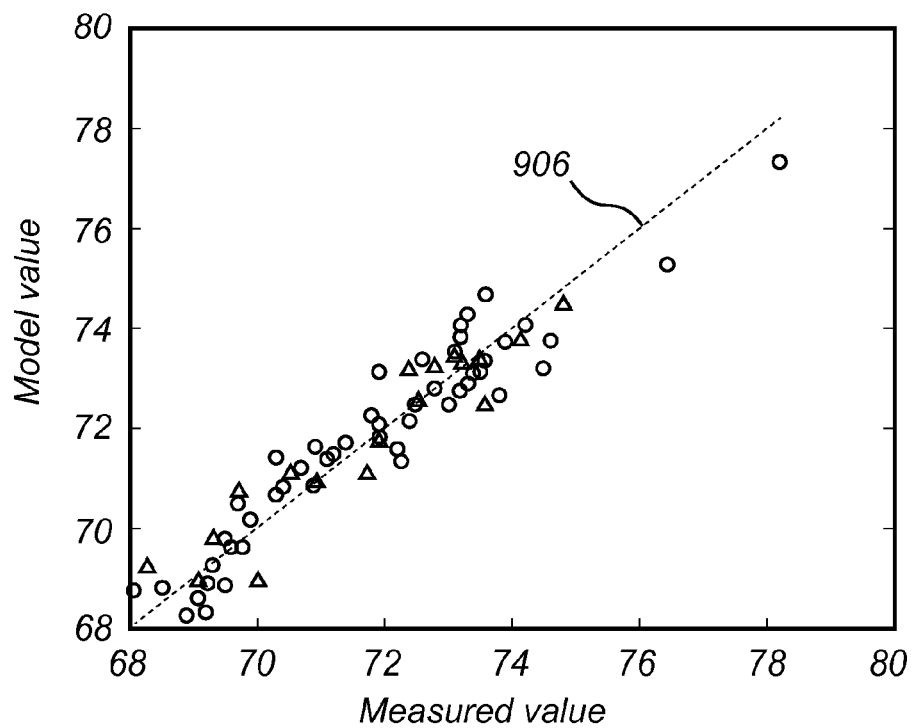

To validate the model, the model data is compared with further samples from the process as illustrated in FIG. 9c. Each circle and triangle in FIG. 9c represents a measurement event involving measuring the value of the fluid property using the conventional non-acoustic method and predicting the value of the fluid property using the model. The circles represent measurement events forming part of the calibration procedure, and the triangles represent measurement events used for validating the model. On the x-axis are the reference measurements and on the y-axis the predictions based on the derived model. The dotted line 904 illustrates an ideal correlation and as can be seen from the data points, there is a high degree of correlation between the model values and the reference values, indicating an accurate model.

Figure 9D:
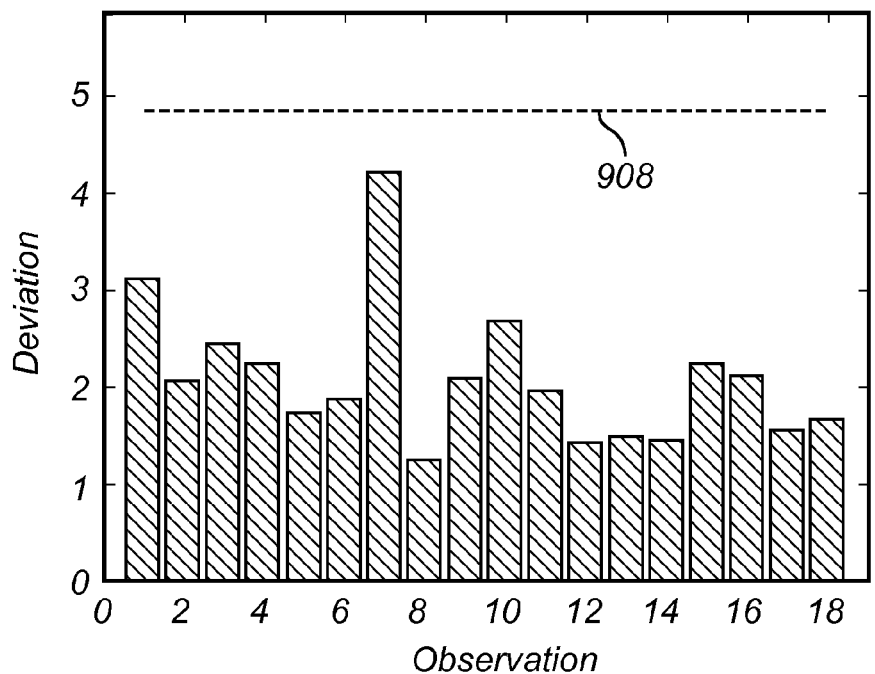

Next, it is evaluated if the deviation between the reference validation fluid property values obtained using the conventional non-acoustic method and the fluid property values estimated based on acoustic measurements using the model is sufficiently small for the particular property of the fluid and the particular process. FIG. 9d illustrates the determined deviation for different specific observations and an upper boundary 908 for the deviation is set. If the deviation is deemed to be too large, the model needs to be refined which is typically done by taking more samples and redoing calibration and validation.

Figure 9E:
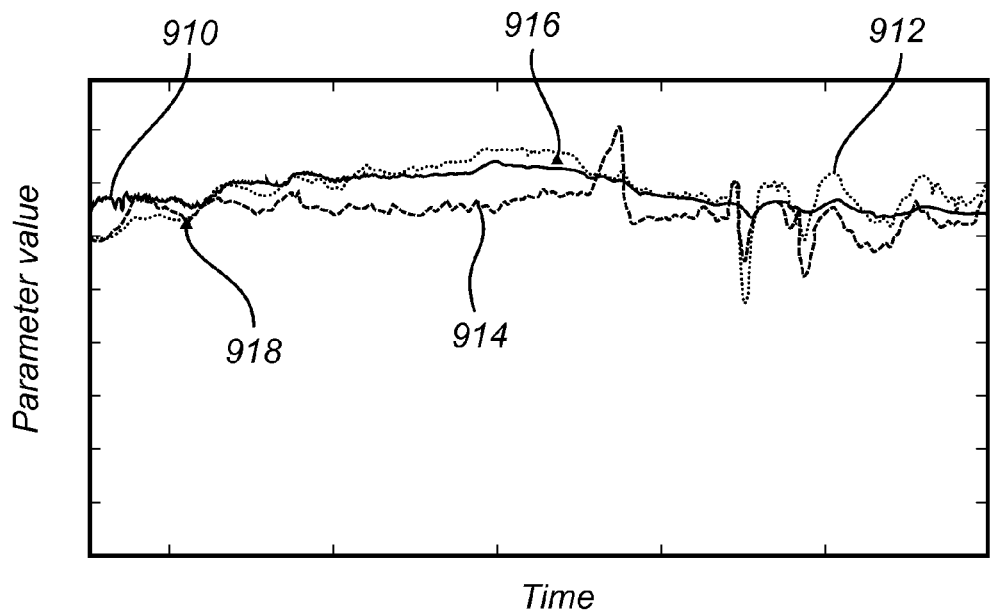

To further validate the model, acoustic spectra (each being provided as a vector of amplitude values) received at regular intervals were then input to the model, and the output of the model is a predicted value of the fluid property as a function of time. The diagram in FIG. 9e shows a first curve 910 (solid) representing the predicted fluid property values, a second curve 912 (dotted) representing fluid property values measured with the conventional non-acoustic method, here an optical refractometer, and a third curve 914 (dashed) representing theoretically calculated values of the fluid property. Two manually acquired laboratory sample are also illustrated as triangles 916, 918, and it can be seen that there is a good correlation between the acoustic measurements using the derived model and the reference measurements. The reference measurements may for example be acquired, during a limited period of time for validation of the established model, using optical refractometers or radioactive gamma radiation detectors of the process on site.

As a further example of the above discussed method, determination of the specific surface area of particles in a colloidal silicon sol will be described where a model is derived using the general steps outlined above. The specific surface area of the particles is given by the relation:

$$A_d = \frac{6 \times 10^2}{ρ \times d_s}, \qquad \text{Equation 3}$$

where $A_d$ is the specific surface area, $d_s$ is the particle diameter of a particle with a specific surface area corresponding to the average surface area of the particles, and ρ is the density.

As a first step before any determination of the specific surface area of the particles can be carried out based on acquired acoustic spectra, the model is established as described above. In this particular example, a series of (physical) samples of the silicon sol are taken. For each sample taken, an acoustic spectrum is acquired, preferably at the same time as the sample is taken. The specific surface area of the particles in the samples taken is determined using conventional analysis, such as through so-called Sears titration. This is a well-known empirical method for determining the surface area of colloidal silicon through titration of the silicon sol with NaOH.

A model is then established as generally described above by correlating the specific surface area values of the samples determined using Sears titration with the corresponding acoustic spectra. This procedure may also be referred to as "calibration". As was generally described above, the calibration correlation is carried out in two steps. First, Principal Component Analysis (PCA) is performed separately on the acoustic spectra and on the lab results obtained using Sears titration.

After having removed the deviating samples that were identified using PCA, the PLS-method is used to identify a relation between the acoustic spectra and the corresponding lab results. The result is an empirical statistical model that can be used to determine the specific surface area of the particles in the silicon sol based on an acquired acoustic spectrum.

Figure 10:
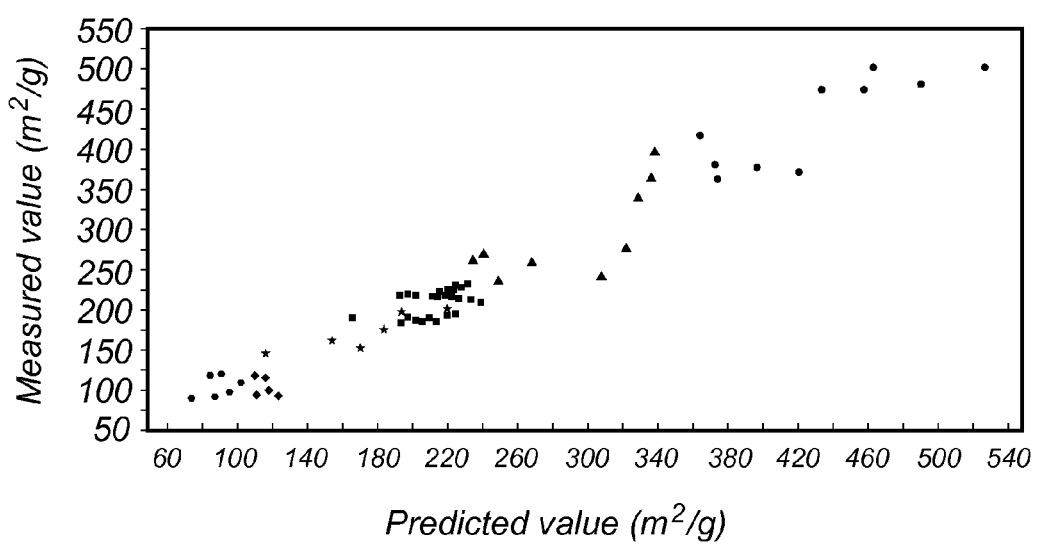
FIG. 10 is a diagram illustrating an example of an applied model according to an embodiment of the invention.

As a further illustration of the applied model, FIG. 10 is a diagram showing predicted values of the specific surface area versus values determined based on acquired acoustic samples and the statistical model set up using PLS. The predicted values using the model are on the x-axis and the observed values (laboratory results) are on the y-axis, and also here the linear relationship indicates a good correlation between the predicted value and the measured reference values.

To improve the signal-to-noise ratio of the received signal, it may be undesirable noise may be removed from the received acoustic signal. In particular, frequencies in the received signal below 5 kHz are sometimes discarded since the lower end of the frequency range is known to have a lower signal-to-noise ratio. In other words, at least a portion of passive noise originating from application specific features can be separated from the received signal by removing frequencies below 5 kHz from the received signal. A suitable cut-off frequency for noise reduction is preferably determined for each specific application and installation.

In practice, noise reduction may be achieved by first determining where in the acoustic spectrum the background signal is strong. Based on this determination (or previous knowledge about the particular system), a portion of the acoustic spectrum can be disregarded when the empirical statistical model is established and when predictions are carried out.

Figure 11A:
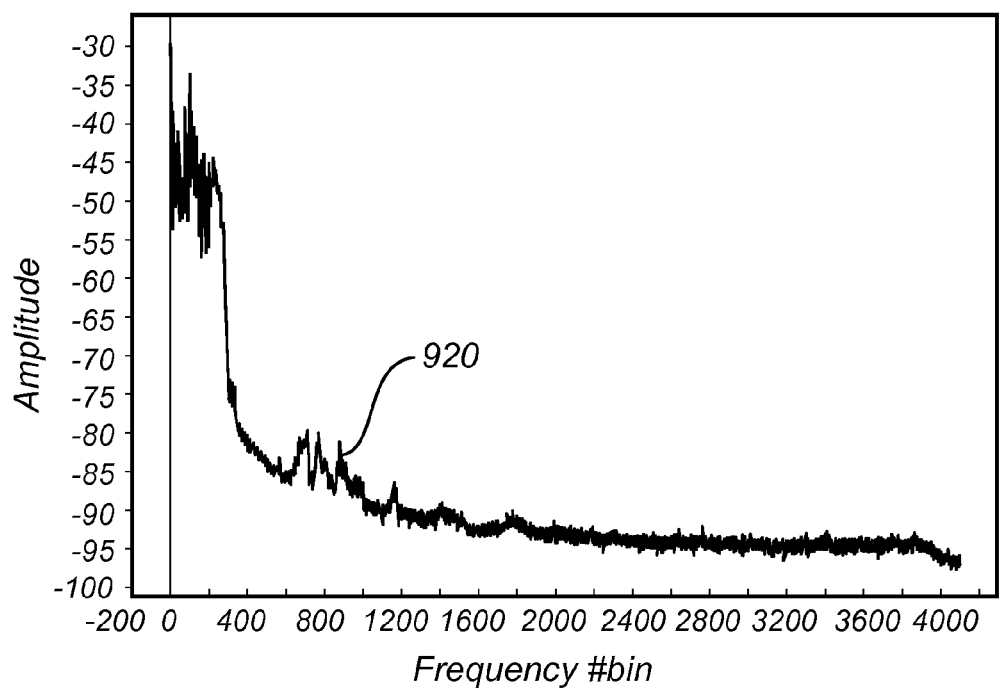
FIGS. 11a-11c are diagrams illustrating noise reduction according to an example embodiment of the invention.

FIG. 11a illustrates a passive spectrum 920 from a particular application, i.e. the acoustic signal generated by the process itself where the x-axis 0-4096 represents 0-48 kHz and the y-axis represents the amplitude in arbitrary units.

Figure 11B:
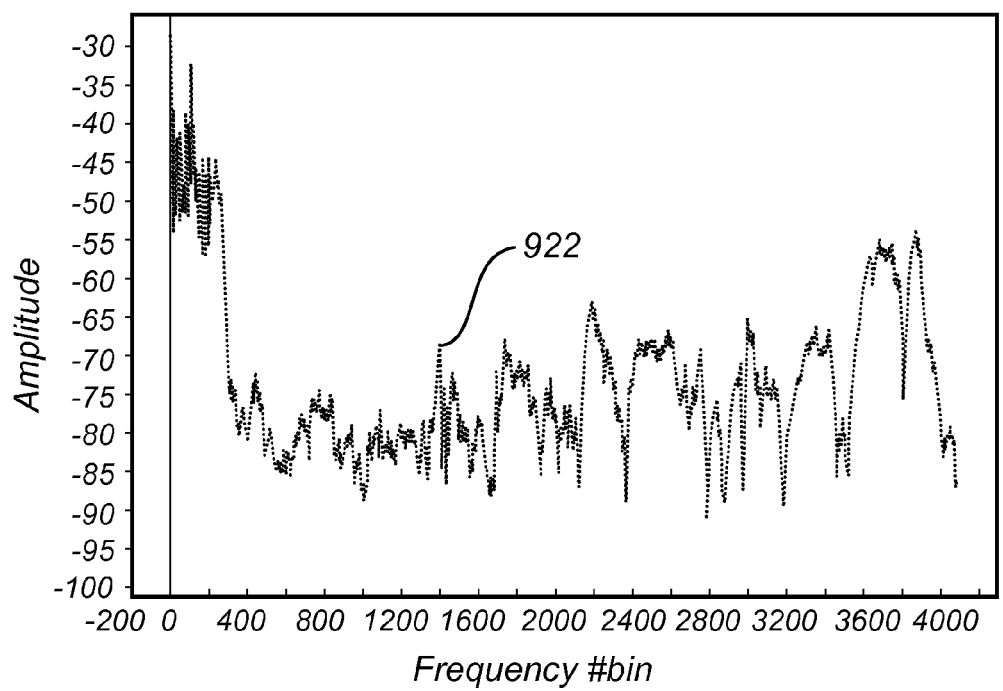

FIG. 11b shows the active spectrum 922, i.e. the spectrum obtained when an acoustic signal is transmitted into the process fluid through the wall of the pipe. The spectrum in FIG. 11b is thus the sum of the passive acoustic signal generated by the process itself and the active acoustic signal generated by the transmitter and modified by passage through the process fluid.

Figure 11C:
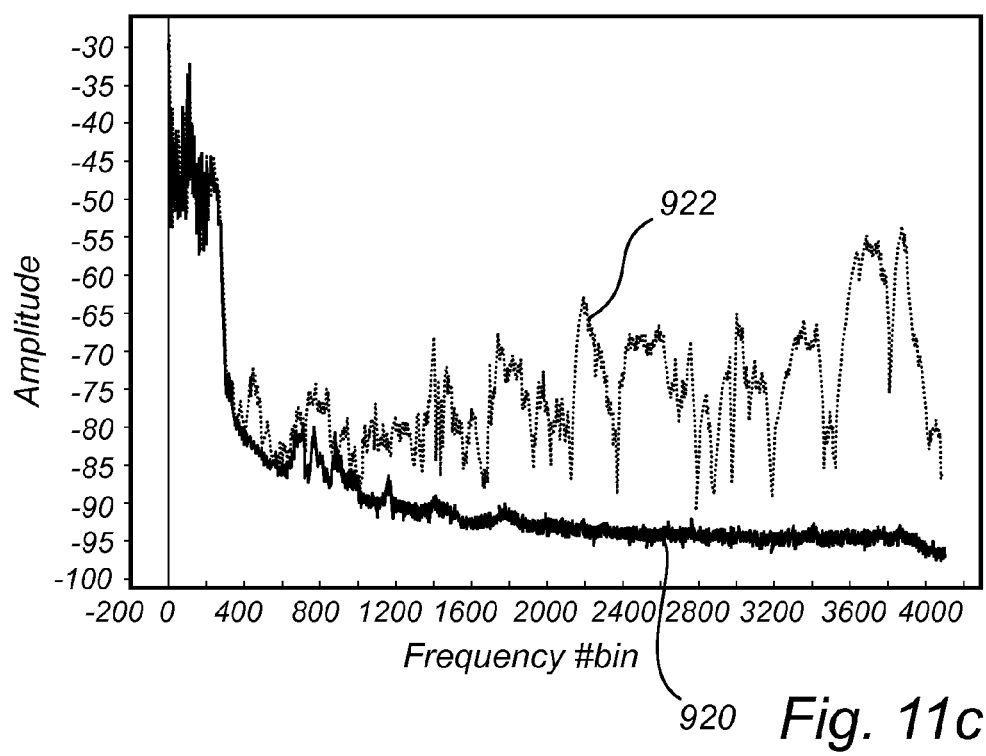

By comparing the passive spectrum 920 in FIG. 11a with the active spectrum 922 of FIG. 11b, as illustrated in FIG. 11c, it can be seen that the background acoustic signal generated by the process itself is negligible compared to the signal resulting from the interaction between the transmitted acoustic signal and the process fluid for frequencies above about 5 kHz, i.e. approximately above sample 400 in FIGS. 11a-11c. Accordingly, in the implementation illustrated in FIGS. 11a-11c, the received signals resulting from the interaction between the actively transmitted acoustic signal and the process fluid are separated from the background signal by disregarding frequencies lower than 5 kHz in the received signal used for further analysis.

The method according to the present invention may be implemented as software, hardware, or a combination thereof. A computer program product implementing the method or a part thereof comprises a software or a computer program run on a general purpose or specially adapted computer, processor or microprocessor. The software includes computer program code elements or software code portions that make the computer perform the method using at least one of the steps previously described in FIG. 6. The program may be stored in whole or part, on, or in, one or more suitable computer readable media or data storage means such as a magnetic disk, CD-ROM or DVD disk, hard disk, magneto-optical memory storage means, in RAM or volatile memory, in ROM or flash memory, as firmware, or on a data server.

It will be understood by those skilled in the art that various modifications and changes may be made to the present invention without departure from the scope thereof, which is defined by the appended claims.

REFERENCES

D. J. Adams: "Ultrasonic propagation in paper fiber suspensions", 3rd International IFAC Conference on Instrumentation and Automation in the Paper, Rubber and Plastics Industries, p. 187-194, Noordnederlands Boekbedrijf, Antwerp, Belgium.

M. Karras, E. Harkonen, J. Tornberg and O. Hirsimaki: "Pulp suspension flow measurement using ultrasonics and correlation", 1982 Ultrasonics Symposium Proceedings, p. 915-918, vol. 2, Ed: B. R. McAvoy, IEEE, New York, N.Y., USA.

French patent FR 2 772 476.

International patent application WO 99/15890.

H. Martens and T. Naes: "Multivariate Calibration", John Wiley & Sons, Chicester, 1989, pp. 116-163.

The invention claimed is:

1. A method for predicting properties of a process fluid flowing in a pipe, the process fluid being a suspension of solid particles or an emulsion of gas or liquid volumes, wherein the properties are based on particles or volumes size distribution and concentration the method comprising:
    emitting a controllable acoustic signal from an acoustic emitter attached to the outer side of the pipe into said process fluid for interaction with the volumes or the particles, said acoustic emitter connected to a controller to control the acoustic signal by frequency, amplitude, phase or timing with the acoustic signal comprising audible frequencies below 20 kHz and wavelengths larger than the sizes of the particles or volumes;
    tuning the controllable acoustic signal with the controller to enhance acoustic response of the particles or volumes in the process fluid;
    measuring acoustic spectrum resulted from modified acoustic signals emitted from the emitter and acoustic signals emitted from the particles or volumes with at least one acoustic sensor, wherein the measurement is made for corresponding amplitudes, phase, time or spatial dependencies of resulting acoustic signals, and wherein the at least one acoustic sensor is attached to the outer side of the pipe apart from the acoustic emitter;
    processing the resulting acoustic spectrum to correlate the measured acoustic spectrum to properties, content or distribution of the particles or volumes within the process fluid with a processor connected to the at least one sensor and the controller, wherein the processor utilizes a predetermined model,
    wherein the predetermined model is developed by correlating acoustic measurements for a known process liquid with corresponding properties of the known process fluid obtained by non-acoustic methods using a multivariate statistical analysis.

2. The method according to claim 1, wherein said step of correlating comprises:
    applying a partial least squares analysis to a sequence of non-acoustic measurements and a sequence of acoustic spectra.

3. The method according to claim 2, wherein said step of correlating further comprises:

removing non-relevant frequencies of said acoustic spectra with low correlation with said non-acoustic measurements.

4. The method according to claim 1, wherein said step of correlating comprises:
performing principal component analysis separately on said acoustic spectrum and on said non-acoustic measurements.

5. The method according to claim 1, wherein said acoustic emitter is smaller than the wavelength of the emitted acoustic signal.

6. The method according to claim 1, wherein said at least one acoustic sensor are two acoustic sensors, separated in a direction along a flow path of the process fluid by a distance smaller than the wavelength of the emitted acoustic signal, and wherein the method further comprises measuring the propagation speed of the acoustic signals within the flowing process fluid or its flow rate.

7. The method according to claim 1, wherein said at least one acoustic sensor are two acoustic sensors separated substantially perpendicularly to a flow path of the flowing process fluid.

8. An analyzing apparatus for performing the method of claim 1, said analyzing apparatus comprising:
an acoustic emitter capable of emitting audible frequencies below 20 kHz, attached to the outer side of the pipe with the flowing process fluid;
at least one acoustic sensor attached at the same side of the pipe and at a distance from the acoustic emitter along the pipe;
a processor, and
a controller connected to said acoustic emitter, said at least one acoustic sensor, and said processor, wherein said controller is arranged and configured to:
control said acoustic emitter to emit a controllable acoustic signal from the acoustic emitter into the process fluid for interaction with the volumes or the particles in the process fluid, wherein the controller controls the acoustic signal by frequency, amplitude, phase and/or timing with the acoustic signal comprising audible frequencies below 20 kHz and wavelengths larger than the sizes of the particles or volumes;
tune the controllable acoustic signal to enhance acoustic response of the particles or volumes in the process fluid;
control the at least one acoustic sensor for measuring acoustic spectrum resulted from modified acoustic signals emitted from the acoustic emitter and acoustic signals emitted from the particles or volumes, wherein the acoustic sensor measures corresponding amplitudes, phase, time or spatial dependencies of resulting acoustic signals;
control the processor connected to the at least one acoustic sensor and the controller to process the resulting acoustic spectrum to correlate the measured acoustic spectrum to the properties of the flowing process fluid based on size distribution and concentrations of the particles or volumes within the process fluid, wherein the processor utilizes a predetermined model, wherein the predetermined model is developed by correlating acoustic measurements for a known process liquid with corresponding properties of the known process fluid obtained by non-acoustic methods using a multivariate statistical analysis.

9. The apparatus according to claim 8, wherein said acoustic emitter is smaller than the wavelength of the emitted acoustic signal.

10. The apparatus according to claim 8, wherein said at least one acoustic sensor are two acoustic sensors, separated in a direction along a flow path of the process fluid by a distance smaller than the wavelength of the emitted acoustic signal.

11. The apparatus according to claim 8, wherein said at least one acoustic sensor are two acoustic sensors separated substantially perpendicularly to a flow path of the process fluid.

* * * * *